(12) United States Patent
Reddy et al.

(10) Patent No.: US 9,657,037 B2
(45) Date of Patent: May 23, 2017

(54) PYRROLE COMPOUNDS WITH SILICON INCORPORATION

(71) Applicant: COUNCIL OF SCIENTIFIC AND INDUSTRIAL RESEARCH, New Delhi (IN)

(72) Inventors: Dumbala Srinivasa Reddy, Maharashtra (IN); Natarajan Vasudevan, Maharashtra (IN); Sachin Bhausaheb Wagh, Maharashtra (IN); Remya Ramesh, Maharashtra (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/895,710

(22) PCT Filed: Jun. 2, 2014

(86) PCT No.: PCT/IN2014/000371
§ 371 (c)(1),
(2) Date: Dec. 3, 2015

(87) PCT Pub. No.: WO2014/195970
PCT Pub. Date: Dec. 11, 2014

(65) Prior Publication Data
US 2016/0115181 A1      Apr. 28, 2016

(30) Foreign Application Priority Data

Jun. 3, 2013 (IN) ............ 1663/DEL/2013

(51) Int. Cl.
*C07F 7/08* (2006.01)

(52) U.S. Cl.
CPC .................... *C07F 7/0816* (2013.01)

(58) Field of Classification Search
CPC ....................................... C07F 7/0816
See application file for complete search history.

(56) References Cited

U.S. PATENT DOCUMENTS 7,763,602 B2    7/2010   Arora et al.

FOREIGN PATENT DOCUMENTS

WO       2013/054275 A1    4/2013

OTHER PUBLICATIONS

International Search Report and Written Opinion dated Aug. 11, 2014 for corresponding International Patent Application No. PCT/IN2014/00371, filed Jun. 2, 2014.
Biava M et al: "New pyrrole derivatives as antimycobacterial agents analogs of BM212", Bioorganic & Medicinal Chemistry Letters, Pergamon, Amsterdam, NL, vol. 9, No. 20, Oct. 18, 1999 (Oct. 18, 1999), pp. 2983-2988, XP025669500.

*Primary Examiner* — Shawquia Jackson
(74) *Attorney, Agent, or Firm* — Merchant & Gould P.C.

(57) ABSTRACT

The present invention discloses novel Silicon incorporated pyrrole compounds of Formula I having potential antibacterial properties. The invention further discloses a process for synthesis of pyrrole compounds with silicon incorporation of Formula I and to the pharmaceutical composition thereof.

9 Claims, No Drawings

PYRROLE COMPOUNDS WITH SILICON INCORPORATION

This application is a 371 National Stage Application of International Application No. PCT/IN2014/000371, filed 2 Jun. 2014, which claims benefit of Serial No. 1663/DEL/2013, filed 3 Jun. 2013 in India and which applications are incorporated herein by reference. To the extent appropriate, a claim of priority is made to each of the above disclosed applications.

The following specification particularly describes the invention and the manner in which it is to be performed.

FIELD OF THE INVENTION

The present invention relates to novel Silicon incorporated pyrrole compounds of Formula I. The present invention also relates to the novel silicon incorporated pyrrole compounds having potential anti-tubercular activity. The invention further relates to process for synthesis of novel pyrrole compounds with silicon incorporation of Formula I and to the pharmaceutical composition thereof.

BACKGROUND AND PRIOR ART OF THE INVENTION

*Tuberculosis* (TB) is an infectious disease caused by *Mycobacterium tuberculosis* (MTB) which is comparatively difficult to control and responsible for a high death-rate in both industrialized and developing countries. TB is a contagious disease, which usually runs a protracted course, ending in death in majority of the cases, with relapse being a common feature of the disease. It is one of the most important causes of prolonged disability and chronic ill health. Drugs such as isoniazid, rifampicin, pyrazinamide, ethambutol streptomycin, para-amino salicylic acid, ethionamide, cycloserine, capreomycin, kanamycin, thioacetazone etc. have been and are being currently used to treat TB. Amongst these, isoniazid, rifampicin, ethambutol and pyrazinamide are the first-line drugs of choice, which are administrated either as a single drug formulation or as a fixed-dose combination of two or more of the aforesaid drugs. Even though, these first-line drug regimens are highly effective for treatment of TB, however, they are associated with shortcomings, such as unpleasant side-effects and relatively long course of treatment. The latter one results in non-compliance of the patient to the treatment leading often to failure of the treatment and most importantly, development of drug resistance.

The emergence of drug resistant pathogens renders the current treatment very difficult and in many cases completely ineffective. Treatment of multi-drug resistant varieties of *tuberculosis* is difficult, and the disease often carries a high rate of mortality, particularly in developing countries. Another problem with current *tuberculosis* therapies is the shift of *M. tuberculosis* into a dormant or latent state. Thus, while the treatment of active *tuberculosis* with the currently prescribed combination drug regimen reduces the bacterial burden by a substantial amount, a proportion of bacilli shift into dormancy and survive in the host for months or years without producing any overt disease. However, later the bacilli can reactivate resulting in active *tuberculosis* once again. The recurrence of, *tuberculosis* these days is considered to be the result of the reactivation of latent organisms which survive in the host [Stead, W W., Am. Rev. Respir. Dis., 1982, 95, 729-745. Stead, W W., Kerby, G R., Schleuter, and Jordahl, C W., Ann. Intern. Med., 1968, 68, 731-745.

The recent recrudescence of TB, due in particular to the increased incidence of the *M. avium* complex MAC infection in HIV-infected individuals, has prompted a vigorous search for new drugs for the treatment of the disease. In fact, the progressive immunological deterioration associated with AIDS is often accompanied by opportunistic infections causing TB (*M. tuberculosis*), a non-TB (*M. avium*) mycobacterial disease and mycotic infections caused by *Candida albicans* and *Cryptococcus neoformans*. Treatment of these infections, along with other opportunistic infections which cause the majority of all AIDS-related deaths, is often complicated by patient intolerance to the drugs employed or pathogen resistance to conventional drug therapy. To meet the challenges of frequent multi-drug resistant tubercular strains of *Mycobacterium tuberculosis* and the growing importance of non-*tuberculosis* mycobacterial (NTM) strains in infections of immunosuppressed patients, search for novel active compounds is of paramount importance. Accordingly, several heterocyclic compounds containing the imidazole, pyrrole, or methanamine group have been tested and developed to treat the potent and selective mycobacterial diseases. Among them, pyrrole derivatives appear to show potent and selective anti-mycobacterial activities. Article titled, "Bactericidal Activities of the Pyrrole Derivative BM212 against Multidrug-Resistant and Intramacrophagic *Mycobacterium tuberculosis* Strains" by Delia Deidda, Giorgio Lampis et. al in Antimicrob Agents Chemother. November 1998; 42(11); 3035-3037 disclosed pyrrole derivative BM212 [1,5-diaryl-2-methyl-3-(4-methylpiperazin-1-yl)methyl-pyrrole] of formula D possessing strong inhibitory activity against both *Mycobacterium tuberculosis* and some non-*tuberculosis* mycobacteria. BM212 is reported to exert bactericidal activity against intracellular bacilli residing in the U937 human histiocytic lymphoma cell line.

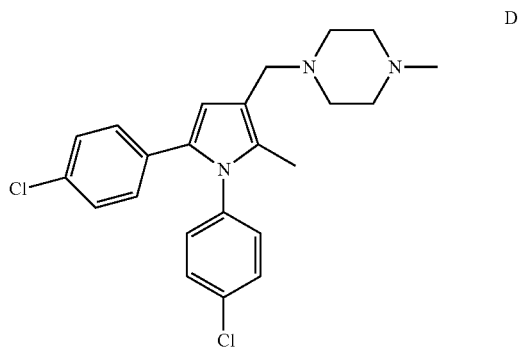 [SMILES: Cc1c(CN2CCN(C)CC2)cc(-c2ccc(Cl)cc2)n1-c1ccc(Cl)cc1]

Article titled, "1,5-Diaryl-2-ethyl pyrrole derivatives as antimycobacterial agents: Design, synthesis, and microbiological evaluation" by Mariangela Biava, Giulio C. Porretta, et.al in European Journal of Medicinal Chemistry (2009; 44; 4734-4738) reports new diaryl pyrroles such as 1-(4-fluorophenyl)-2-ethyl-3-(thiomorpholin-4-yl)methyl-5-(4-methylphenyl)-1H-pyrrole active against *tuberculi* bacteria. U.S. Pat. No. 7,763,602 discloses pyrrole derivatives of formula (I) and their pharmaceutically acceptable acid addition salts having antimycobacterial activity against clinically sensitive as well as resistant strains of *Mycobacterium tuberculosis*.

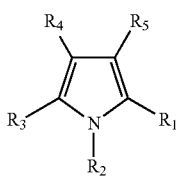

wherein, R1 to R5 are as defined therein. In view to meet the ever growing challenges of multi-drug resistant bacterial infections, in particular multi-drug resistant *Mycobacterium tuberculi* strains in both dormant and latent stages, there is an urgent need to develop newer regimens that can be used to prevent, treat and/or reduce *tuberculosis* and/or eliminate the threat of multi-drug resistant *tuberculosis* and/or latent *tuberculosis*.

OBJECT OF THE INVENTION

The main objective of the present invention is to provide novel silicon incorporated pyrrole compounds of general formula (I). Silicon incorporated molecules are expected to have better pharmacokinetic and pharmacodynamic properties and they also may have better cell-wall penetrating capability.

Yet another objective of the invention is to provide a process to synthesize the silicon incorporated pyrrole compound of Formula (I) with high selectivity, yield.

Yet another object of the present invention is to provide novel silicon incorporated pyrrole compounds of general formula (I) useful for the treatment of *tuberculosis* effective against both active and latent form.

Another objective of the invention is to provide pharmaceutical compositions containing the novel compounds of general formula (I) for treating *tuberculosis* and other related diseases.

SUMMARY OF THE INVENTION

Accordingly the present invention provides a novel silicon incorporated pyrrole compounds of Formula (I) and pharmaceutically acceptable salts thereof.

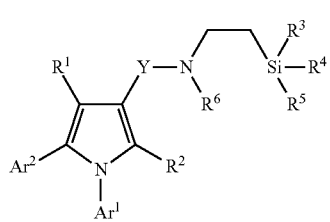

wherein $R^1$ and $R^2$ are selected from hydrogen, halogen, alkyl, haloalkyl, hydroxyalkyl, thioalkyl, aryl, heteroaryl, C1-C5 alkoxy, C1-C5 alkoxyalkyl, —NR'R", —CH$_2$NR'R"—CONR'R", —COOR'";
R', R" are independently selected from hydrogen or alkyl, aryl which may be substituted or unsubstituted or R' and R" together may form a ring up to six carbon atoms which optionally may be substituted and/or may contain hetero atoms;
R'" is selected from hydrogen or alkyl, aryl which may be substituted or unsubstituted; $R^3$, $R^4$ and $R^5$ each are individually selected from C1 to C12 alkyl, aryl, heteroaryl, aralkyl, halogen or any two of $R^3$, $R^4$ and $R^5$ may form 4-8 member ring which optionally may be further substituted and/or may contain additional hetero atoms; $R^6$ is selected from hydrogen, C1 to C12 alkyl, aryl, heteroaryl, aralkyl or $R^6$ together with any of $R^3$, $R^4$ and $R^5$ may form a ring;
$Ar^1$ and $Ar^2$ represent independently a aryl or heteroaryl unsubstituted, or substituted with one or more substituents selected independently from halo, hydroxy, alkyl, aralkyl, cycloalkyl, alkoxy, alkylthio, alkyl sulfinyl, alkyl sulfonyl, heterocyclyl, aryl, nitro, sulfonyl, —NR'R", —CONR'R", —COOR'" wherein positions of substituent $Ar^2$ and $R^2$ are interchangeable; Y represents CO, CS, CONH or $CR^1R^2$; wherein $R^1R^2$ are independently selected from hydrogen or alkyl, aryl which may which may be substituted or unsubstituted; or $R^1$ and $R^2$ together form a ring up to six carbon atoms which optionally may be substituted and/or may contain hetero atoms.

In an embodiment of the present invention, the novel silicon incorporated pyrrole compounds of Formula (I) are selected from the group consisting of
a) (1,5-bis(4-chlorophenyl)-2-methyl-1H-pyrrol-3-yl)(4,4-dimethyl-1,4-azasilinan-1-yl)methanone of formula (5);
b) 1-((1,5-bis(4-chlorophenyl)-2-methyl-1H-pyrrol-3-yl) methyl)-4,4-dimethyl-1,4-azasilinane of formula (9);
c) 1-((1-(4-fluorophenyl)-2-methyl-5-(4-(methylthio)phenyl)-1H-pyrrol-3-yl)methyl)-4,4-dimethyl-1,4-azasilinane (10a);
d) 1-((1-(4-fluorophenyl)-5-methyl-2-(4-(methylthio)phenyl)-1H-pyrrol-3-yl)methyl)-4,4-dimethyl-1,4-azasilinane (10b);
e) 1-((1-(4-chlorophenyl)-5-(4-isopropylphenyl)-2-methyl-1H-pyrrol-3-yl)methyl)-4,4-dimethyl-1,4-azasilinane (11a);
1-((1-(4-isopropylphenyl)-2-methyl-5-(4-(methylthio)phenyl)-1H-pyrrol-3-yl)methyl)-4,4-dimethyl-1,4-azasilinane (12a);
g) 1-((1-(4-isopropylphenyl)-5-methyl-2-(4-(methylthio) phenyl)-1H-pyrrol-3-yl)methyl)-4,4-dimethyl-1,4-azasilinane (12b);
h) 1-((5-(4-chlorophenyl)-1-(4-ethylphenyl)-2-methyl-1H-pyrrol-3-yl)methyl)-4,4-dimethyl-1,4-azasilinane (13);
i) 1-((1-(4-fluorophenyl)-2-(4-methoxyphenyl)-5-methyl-1H-pyrrol-3-yl)methyl)-4,4-dimethyl-1,4-azasilinane (14);
j) 1-((5-(4-chlorophenyl)-2-methyl-1-phenyl-1H-pyrrol-3-yl)methyl)-4,4-dimethyl-1,4-azasilinane (15);
k) 1-((5-(4-ethylphenyl)-1-(4-methoxyphenyl)-2-methyl-1H-pyrrol-3-yl)methyl)-4,4-dimethyl-1,4-azasilinane (16);
l) 1-((1-(4-fluorophenyl)-2-methyl-5-(p-tolyl)-1H-pyrrol-3-yl)methyl)-4,4-dimethyl-1,4-azasilinane (17);
m) 1-((2-(4-ethoxyphenyl)-1-(4-methoxyphenyl)-5-methyl-1H-pyrrol-3-yl)methyl)-4,4-dimethyl-1,4-azasilinane (18);
n) 1-((5-(4-chlorophenyl)-1-(4-isopropylphenyl)-2-methyl-1H-pyrrol-3-yl)methyl)-4,4-dimethyl-1,4-azasilinane (19).

In still another embodiment of the present invention, the silicon incorporated pyrrole compounds of Formula (I) are useful for the treatment of *tuberculosis*

In yet another embodiment of the present invention, compound of Formula (I), are useful against *Mycobacterium tuberculi* both in dormant or latent phase.

In still another embodiment of the present invention, a process for preparation of novel pyrrole compounds with silicon incorporation of Formula (I), comprising; peptide coupling of compound of formula A,

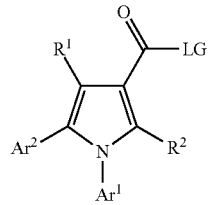

A wherein R¹ and R² are selected from hydrogen, halogen, alkyl, haloalkyl, hydroxyalkyl, thioalkyl, aryl, heteroaryl, C1-C5 alkoxy, C1-C5 alkoxyalkyl, —NR'R", —CH₂NR'R"—CONR'R", —COOR'";

R', R" are independently selected from hydrogen or alkyl, aryl which may be substituted or unsubstituted or R' and R" together may form a ring up to six carbon atoms which optionally may be substituted and/or may contain hetero atoms;

R'" is selected from hydrogen or alkyl, aryl which may be substituted or unsubstituted;

Ar¹ and Ar² represent independently a aryl or heteroaryl unsubstituted, or substituted with one or more substituents selected independently from halo, hydroxy, alkyl, aralkyl, cycloalkyl, alkoxy, alkylthio, alkyl sulfinyl, alkyl sulfonyl, heterocyclyl, aryl, nitro, sulfonyl, —NR'R", —CONR'R", —COOR'" wherein positions of substituent Ar² and R² are interchangeable;

LG represent the leaving group selected from —OH, halogen, anhydride etc;

with an amine of formula B

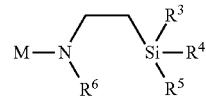

B wherein, M is selected from H or —NH2;

R³, R⁴ and R⁵ each are individually selected from C1 to C12 alkyl, aryl, heteroaryl, aralkyl, halogen or any two of R³, R⁴ and R⁵ may form 4-8 member ring which optionally may be further substituted and/or may contain additional hetero atoms; R⁶ is selected from hydrogen, C1 to C12 alkyl, aryl, heteroaryl, aralkyl or R⁶ together with any of R³, R⁴ and R⁵ may form a ring;

in presence of a coupling agent, HOBt, a base and solvent at a temperature in the range of 55-65° C.

In yet another embodiment of the present invention, the process for preparation of novel pyrrole compounds with silicon incorporation of Formula (I), comprising;
reacting pyrrole compound of Formula C

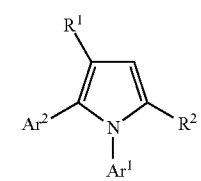

C

Wherein, R¹ and R² are selected from hydrogen, halogen, alkyl, haloalkyl, hydroxyalkyl, thioalkyl, aryl, heteroaryl, C1-C5 alkoxy, C1-C5 alkoxyalkyl, —NR'R", —CH₂NR'R"—CONR'R", —COOR'";

R', R" are independently selected from hydrogen or alkyl, aryl which may be substituted or unsubstituted or R' and R" together may form a ring up to six carbon atoms which optionally may be substituted and/or may contain hetero atoms; R'" is selected from hydrogen or alkyl, aryl which may be substituted or unsubstituted;

Ar¹ and Ar² represent independently a aryl or heteroaryl unsubstituted, or substituted with one or more substituents selected independently from halo, hydroxy, alkyl, aralkyl, cycloalkyl, alkoxy, alkylthio, alkyl sulfinyl, alkyl sulfonyl, heterocyclyl, aryl, nitro, sulfonyl, —NR'R", —CONR'R", —COOR'" wherein positions of substituent Ar² and R² are interchangeable;

with a compound of formula B;

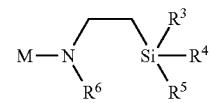

B wherein, M is selected from H or —NH2;

R³, R⁴ and R⁵ each are individually selected from C1 to C12 alkyl, aryl, heteroaryl, aralkyl, halogen or any two of R³, R⁴ and R⁵ may form 4-8 member ring which optionally may be further substituted and/or may contain additional hetero atoms;

R⁶ is selected from hydrogen, C1 to C12 alkyl, aryl, heteroaryl, aralkyl or R⁶ together with any of R³, R⁴ and R⁵ may form a ring;

in presence of formaldehyde, base and a solvent at room temperature for about 16 to 18 hours.

In still another embodiment of the present invention, the coupling agent is selected from N,N'-Dicyclohexylcarbodiimide (DCC), 1-Ethyl-3-(3-dimethylaminopropyl)carbodiimide (EDC), HATU (O-(7-azabenzotriazol-1-yl)-N,N,N',N'-tetramethyluronium hexafluorophosphate), HBTU (O-Benzotriazole-N,N,N',N'-tetramethyl-uronium-hexafluoro-phosphate) and the like.

In yet another embodiment of the present invention, the base is selected from diisopropylethylamine triethylamine, pyridine and the like.

In still another embodiment of the present invention, the solvent is selected from polar protic or aprotic solvents either alone or mixtures thereof.

In yet another embodiment of the present invention, the pharmaceutical composition comprising a pharmaceutically acceptable excipient and an effective amount of compound of formula (I), for the treatment of *tuberculosis*.

In another aspect, the present invention provides a pharmaceutical composition comprising a therapeutically effective amount of a compound of Formula (I) either alone or as its salts, isomers, derivatives along with one or more suitable pharmaceutical carriers/excipients.

DETAILED DESCRIPTION OF THE INVENTION

The present invention relates to novel silicon incorporated pyrrole compounds of Formula (I) and its pharmaceutically acceptable salts having potential anti-bacterial properties comprising;

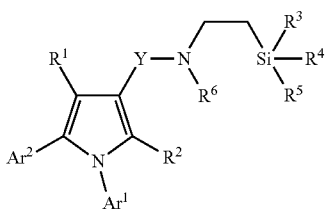

Formula (I)

wherein $R^1$ and $R^2$ are selected from hydrogen, halogen, alkyl, haloalkyl, hydroxyalkyl, thioalkyl, aryl, heteroaryl, C1-C5 alkoxy, C1-C5 alkoxyalkyl, —NR'R", —CH$_2$NR'R"—CONR'R", —COOR'''; R', R" are independently selected from hydrogen or alkyl, aryl which may be substituted or unsubstituted; or R' and R" together may form a ring up to six carbon atoms which optionally may be substituted and/or may contain hetero atoms; R''' is selected from hydrogen or alkyl, aryl which may be substituted or unsubstituted; $R^3$, $R^4$ and $R^5$ each are individually selected from C1 to C12 alkyl, aryl, heteroaryl, aralkyl, halogen or any two of $R^3$, $R^4$ and $R^5$ may form 4-8 membered ring which optionally may be further substituted and/or may contain additional hetero atoms; $R^6$ is selected from hydrogen, C1 to C12 alkyl, aryl, heteroaryl, aralkyl or $R^6$ together with any of $R^3$, $R^4$ and $R^5$ may form a ring;

$Ar^1$ and $Ar^2$ represent independently a aryl or heteroaryl unsubstituted, or substituted with one or more substituent selected independently from halo, hydroxy, alkyl, aralkyl, cycloalkyl, alkoxy, alkylthio, alkyl sulfinyl, alkyl sulfonyl, heterocyclyl, aryl, nitro, sulfonyl, —NR'R", —CONR'R", —COOR''' wherein positions of substituent $Ar^2$ and $R^2$ are interchangeable;

Y represents CO, CS, CONH or CR'R$^2$; wherein R$^1$R$^2$ are independently selected from hydrogen or alkyl, aryl which may which may be substituted or unsubstituted; or $R^1$ and $R^2$ together form a ring up to six carbon atoms which optionally may be substituted and/or may contain hetero atoms. The compounds of formula (I) may be present in the form of salts, isomers, hydrates and derivatives thereof. In another embodiment, the present invention disclose novel silicon incorporated pyrrole compounds of Formula (I) effective against *Mycobacterium tuberculi* and *Mycobacterium avium* in both active and latent form.

The novel silicon incorporated analogues, alter physico-chemical properties, in particular lipophilicity and in-vivo metabolism, which in turn is observed to increase druggable properties [J. Med. Chem. 2013, 56, 388-405; Expert Opin. Investig. Drugs 2004, 13 (9): 1149-1157].

In an embodiment, the present invention provides a process for preparation of novel Si incorporated pyrrole compounds of Formula (I) comprising;
peptide coupling of compound of formula A,

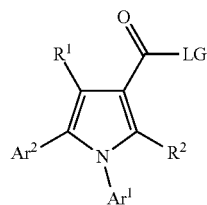

A wherein R1, R2 and Ar1, Ar2 are as defined above;

LG represent the leaving group selected from —OH, halogen, anhydride etc;
with an amine of formula B or optionally its acid salt

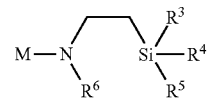

B wherein, M is selected from H or —NH2; R3, R4, R5 and R6 are as defined above. in presence of a coupling agent, HOBt, a base and solvent at a temperature in the range of 55-65° C.

The coupling agent in the process is selected from N,N'-Dicyclohexylcarbodiimide (DCC), 1-Ethyl-3-(3-dimethylaminopropyl)carbodiimide (EDC), HATU (O-(7-azabenzotriazol-1-yl)-N,N,N',N'-tetramethyluronium hexafluorophosphate), HBTU (O-Benzotriazole-N,N,N',N'-tetramethyl-uronium-hexafluoro-phosphate) and the like. The base is selected from diisopropylethylamine, triethylamine, pyridine and the like, preferably triethylamine; the solvent is selected from polar aprotic solvent such as EDC (ethylenedichloride), THF (tetrahydrofuran), DCM (dichloromethane, DMF (dimethylformamide), ethylacetate, acetonitrile and such like either alone or mixtures thereof.

In an alternate embodiment, the present invention provides a process for preparation of novel silicon incorporated pyrrole compounds of Formula I and its pharmaceutically acceptable salts, comprising;
reacting pyrrole compound of Formula C

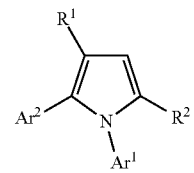

C wherein R1, R2, Ar1 and Ar2 are as defined above;
with a compound of formula B;

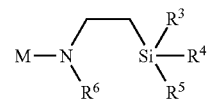

B wherein, M is selected from H or —NH2; R3, R4, R5 and R6 are as defined above;
in presence of formaldehyde, base and a solvent at room temperature for about 16-18 hours.

The base for Mannich condensation reaction is selected from diisopropylethyl amine, triethylamine, pyridine and the like, preferably triethylamine; the solvent is selected from polar protic or aprotic solvent such as acetic acid, lower alcohols, formic acid, EDC, THF, ethyl acetate, acetonitrile and such like either alone or mixtures thereof.

In an embodiment, the present invention provides novel silicon analogues based on pyrrole skeleton selected from;
(1,5-bis(4-chlorophenyl)-2-methyl-1H-pyrrol-3-yl)(4,4-dimethyl-1,4-azasilinan-1-yl)methanone of formula (5);

1-((1,5-bis(4-chlorophenyl)-2-methyl-1H-pyrrol-3-yl)methyl)-4,4-dimethyl-1,4-azasilinane of formula (9);
1-((1-(4-fluorophenyl)-2-methyl-5-(4-(methylthio)phenyl)-1H-pyrrol-3-yl)methyl)-4,4-dimethyl-1,4-azasilinane of formula (10a);
1-((1-(4-fluorophenyl)-5-methyl-2-(4-(methylthio)phenyl)-1H-pyrrol-3-yl)methyl)-4,4-dimethyl-1,4-azasilinane of formula (10b);
1-((1-(4-chlorophenyl)-5-(4-isopropylphenyl)-2-methyl-1H-pyrrol-3-yl)methyl)-4,4-dimethyl-1,4-azasilinane of formula (11a);
1-((1-(4-isopropylphenyl)-2-methyl-5-(4-(methylthio)phenyl)-1H-pyrrol-3-yl)methyl)-4,4-dimethyl-1,4-azasilinane of formula (12a);
1-((1-(4-isopropylphenyl)-5-methyl-2-(4-(methylthio)phenyl)-1H-pyrrol-3-yl)methyl)-4,4-dimethyl-1,4-azasilinane of formula (12b);
1-((5-(4-chlorophenyl)-1-(4-ethylphenyl)-2-methyl-1H-pyrrol-3-yl)methyl)-4,4-dimethyl-1,4-azasilinane of formula (13);
1-((1-(4-fluorophenyl)-2-(4-methoxyphenyl)-5-methyl-1H-pyrrol-3-yl)methyl)-4,4-dimethyl-1,4-azasilinane of formula (14);
1-((5-(4-chlorophenyl)-2-methyl-1-phenyl-1H-pyrrol-3-yl)methyl)-4,4-dimethyl-1,4-azasilinane (15);
1-((5-(4-ethylphenyl)-1-(4-methoxyphenyl)-2-methyl-1H-pyrrol-3-yl)methyl)-4,4-dimethyl-1,4-azasilinane of formula (16);
1-((1-(4-fluorophenyl)-2-methyl-5-(p-tolyl)-1H-pyrrol-3-yl)methyl)-4,4-dimethyl-1,4-azasilinane of formula (17);
1-((2-(4-ethoxyphenyl)-1-(4-methoxyphenyl)-5-methyl-1H-pyrrol-3-yl)methyl)-4,4-dimethyl-1,4-azasilinane of formula (18);
1-((5-(4-chlorophenyl)-1-(4-isopropylphenyl)-2-methyl-1H-pyrrol-3-yl)methyl)-4,4-dimethyl-1,4-azasilinane of formula (19).

In another embodiment, the process for synthesis of compound of formula (5) comprises coupling of compound of formula (4) with 4,4-dimethyl-1,4-azasilinane in presence of EDC, HOBt, triethylamine as base and acetonitrile as solvent at a temperature of 60° C. The compound of formula (5) is obtained from compound of formula (3) which is synthesised by Paal-Knorr condensation of the 1,4-diketone (2) with p-chloroaniline. The process is given below in scheme I.

Scheme-I

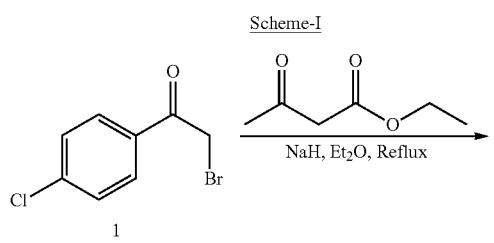

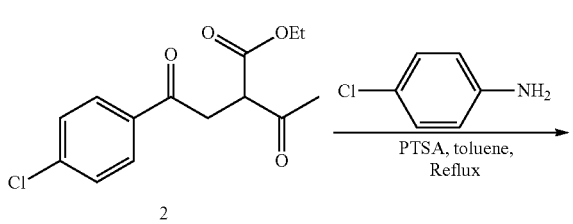

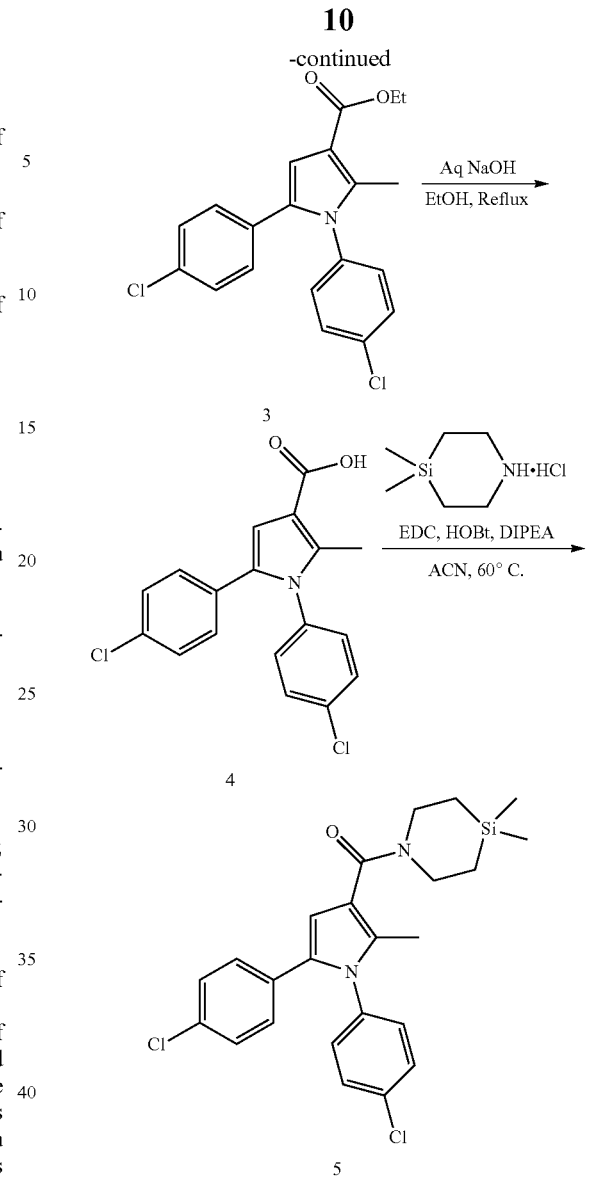

In yet another embodiment, the process for synthesis of compound of formula (9) comprises Mannich condensation of compound of formula (8) with formaldehyde and 4,4-dimethyl-1,4-azasilinane in presence of triethylamine, acetic acid and acetonitrile as solvent at room temperature for about 16 hours. The compound of formula (8) is prepared by the Paal-Knorr condensation of compound of formula (7) with p-chloroaniline. The reaction scheme (II) is given below.

Scheme-II

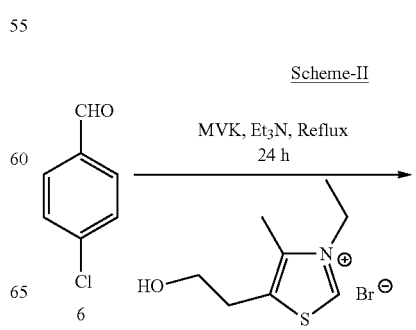

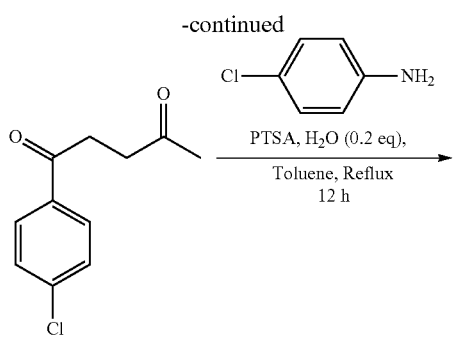

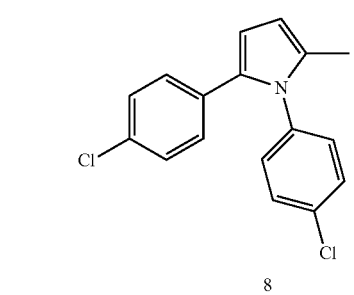

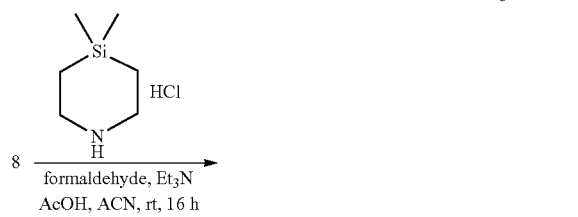

The synthesized compounds of the current invention are further characterized by their spectral data (IR/NMR).

The synthesized pyrrole compounds with silicon incorporation of formula (I) can advantageously be used to treat the pathogens as well as pathological conditions or the diseases caused by *Mycobacterium bacilli* both in dormant and latent stage.

Accordingly, the synthesized compounds of formula (I) are tested for antitubercular activity through inhibition of growth of the virulent strain of *Mycobacterium tuberculosis* H37Rv using Alamar-Blue assay method. The MIC values are given below in Table 1.

In another aspect, the present invention relates to a pharmaceutical composition comprising a therapeutically effective amount of a compound of Formula 1 either alone or as its salts, isomers, derivatives along with one or more suitable pharmaceutical carriers/excipients for the treatment of bacterial infections/diseases.

The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, injections, gels and microspheres, In another embodiment, the present invention relates to administering 'an effective amount' of the 'composition of invention' to the subject suffering from said disease. Accordingly, compound of formula (I) and pharmaceutical compositions containing them may be administered using any amount, any form of pharmaceutical composition via any route of administration effective for treating the disease. Typical routes of administering such pharmaceutical compositions include, without limitation, oral, topical, transdermal, inhalation, parenteral, sublingual, buccal, rectal, vaginal, and intranasal.

Pharmaceutical compositions of the invention are formulated so as to allow the active ingredients contained therein to be bio available upon administration of the composition to a patient. Compositions that will be administered to a subject or patient may take the form of one or more dosage units. The dosage forms can also be prepared as sustained, controlled, modified and immediate dosage forms. The pharmaceutical composition is to be used potentially against *mycobacterium* species including *tuberculosis* and *avium*. The pharmaceutical composition is also useful as antibacterial, antifungal, antiparasitic, antitumor and in treating several CNS related problems like depressions and such like. The compositions may be used against both animals preferably mammals and plants as well. In another embodiment, the present invention provides a method for treating bacterial infections/diseases comprising administering to said subject an effective amount of a compound of formula (I). In yet another embodiment, the present invention provides a method for treating *tuberculosis* caused by *Mycobacterium tuberculi* both in dormant and latent phase comprising administering to said subject an effective amount of a compound of formula (I). The subject as referred herein is a human, animal or plant.

In another embodiment, the present invention discloses use of compound of formula (I) against bacterial infections/diseases.

EXAMPLES

The following examples are given by way of illustration of the present invention and should not be construed to limit the scope of the invention.

Example 1

(1,5-bis(4-chlorophenyl)-2-methyl-1H-pyrrol-3-yl)(4,4-dimethyl-1,4-azasilinan-1-yl)methanone (5)

Ethyl 2-acetyl-4-(4-chlorophenyl)-4-oxobutanoate (2)

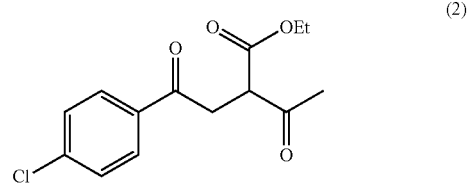 [SMILES: CCOC(=O)C(CC(=O)c1ccc(Cl)cc1)C(C)=O]

Ethyl 3-oxobutanoate 1a (1.2 eq) was drop wise added into slurry of NaH (1.2 eq) in dry diethyl ether (Et₂O, 75 ml) at 0° C., mixture was stirred for 30 min at ambient temperature, then 2-bromo-1-(4-chlorophenyl)ethan-1-one 1 (1 eq, 20 g) in diethyl ether (Et₂O) (100 ml) was added at 0° C., reaction mass was refluxed for 8 h. The solid thus formed was filtered, washed twice with Et₂O (2×35 mL), combined organic layer was evaporated to dryness, purified by silica gel (100-200 mesh) using Ethyl acetate:Pet ether (20:80) as a mobile phase to afford 2 (23.7 g, 98%) light yellow solid. ¹H NMR (200 MHz, CDCl₃): δ 7.86-7.91 (m, 2H), 7.37-7.43 (m, 2H), 4.14-4.25 (m, 3H), 3.47-3.50 (dd, 1H), 3.58-3.63 (dd, 1H), 2.40(s, 3H), 1.22-1.30 (q, 3H); MS: 305 (M+Na)⁺

Ethyl 1,5-bis(4-chlorophenyl)-2-methyl-1H-pyrrole-3-carboxylate (3)

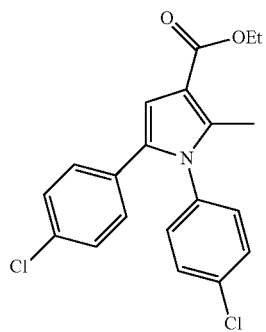

(3)

The mixture of 4-chloroaniline (1.0 eq), 1,4-dione 2 (10 g, 1.2 eq), and catalytic amounts of p-Toluene sulfonic acid monohydrate (2.0 mol %) in toluene (50 ml) was refluxed in a flask equipped with a Dean-Stark apparatus for 8 h. After cooling, the dark-brown reaction mixture was concentrated in vacuo. Purification by flash chromatography provided 3 (11.8 g, 90%) as a off-white solid
¹H NMR (200 MHz, CDCl₃): δ 7.41 (d, 2H), 6.93-7.12 (m, 6H), 6.78 (s, 1H), 4.40-4.33 (q, 2H), 2.39 (s, 3H), 1.33-1.41 (t, 3H); MS: 396 (M+Na)⁺

1,5-bis(4-chlorophenyl)-2-methyl-1H-pyrrole-3-carboxylic acid (4)

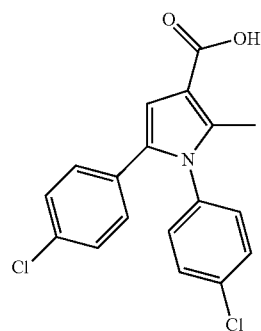

(4)

A mixture of ethyl 1,5-bis(4-chlorophenyl)-2-methyl-1H-pyrrole-3-carboxylate 3 (10 g, 1 eq), and NaOH (5 eq) in EtOH:H₂O (3:1, 100 ml) was refluxed for 16 h. Reaction mass was evaporated to dryness, solid thus formed was dissolved in H₂O (150 ml), acidified with 6N HCl and extracted with ethylacetate (3×150 mL). The combined organic layer was washed with H₂O (50 ml), brine (50 ml), dried over Na₂SO₄ and evaporated to give 4 (8.1 g, 98%) as a white solid. ¹H NMR (200 MHz, CDCl₃): δ 12.05 (bs, 1H), 7.53-7.58 (d, 2H), 7.27-7.34 (m, 4H), 7.04-7.08 (d, 2H), 6.72 (s, 1H), 2.32 (s, 3H); MS: 396 (M+Na)⁺

(1,5-bis(4-chlorophenyl)-2-methyl-1H-pyrrol-3-yl)(4,4-dimethyl-1,4-azasilinan-1-yl)methanone (5)

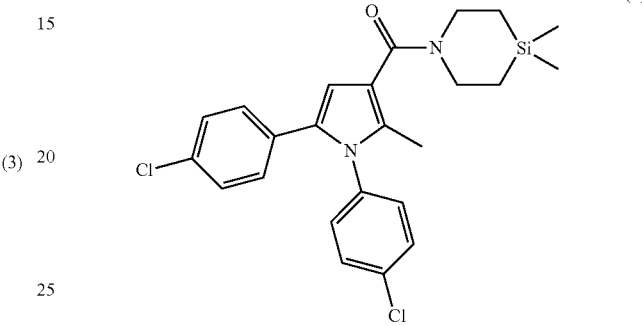

(5)

To a solution of 1,5-bis(4-chlorophenyl)-2-methyl-1H-pyrrole-3-carboxylic acid 4 (400 mg, 1 eq) and 4,4-dimethyl-1,4-azasilinane hydrochloride (1.1 eq) in acetonitrile (5 mL), N-(3-Dimethylaminopropyl)-N'-ethylcarbodiimide hydrochloride (EDC.HCl, 1.2 eq), Hydroxybenzotriazole (HOBt 1.1 eq) and triethylamine (4 eq) were added and stirred for 24 h at 60° C. The reaction mixture was diluted with ethylacetate (30 mL) and washed with 1N HCl (10 mL) and sat. NaHCO₃ solution (10 mL), organic layer was separated, dried over Na₂SO₄, concentrated under reduced pressure and purified by column chromatography (silica gel 230-400, 3:97 methanol:dichloromethane) to afford 5 (310 mg, 28%) as a colorless solid. IR υ$_{max}$(film): cm⁻¹ 2951, 1615, 1494, 1275, 1253, 1090, 842, 751; ¹H NMR (500 MHz, CDCl₃) δ=7.38 (d, J=8.5 Hz, 2H), 7.16 (d, J=8.5 Hz, 2H), 7.10 (d, J=8.5 Hz, 2H), 6.97 (d, J=8.2 Hz, 2H), 6.44 (s, 1H), 3.90-3.79 (m, 4H), 2.21-2.15 (s, 3H), 0.99-0.75 (m, 4H), 0.22-0.10 (m, 6H); ¹³C NMR (126 MHz, CDCl₃) δ=167.5, 136.9, 134.0, 132.4, 132.3, 132.1, 130.9, 129.7, 129.5, 129.1, 128.4, 117.6, 108.7, 12.1, −3.0; MS: 480 (M+Na)⁺

Example 2

1-((1,5-bis(4-chlorophenyl)-2-methyl-1H-pyrrol-3-yl)methyl)-4,4-dimethyl-1,4-azasilinane (9)

1-(4-chlorophenyl) pentane-1,4-dione (7)

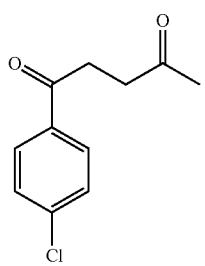

(7)

A mixture of 4-chlorobenzaldehyde 6 (2 g, 1 eq), triethylamine (1.5 eq), Methyl vinyl ketone (1.1 eq), and 3-ethyl-2-(2-hydroxyethyl)thiazol-3-ium bromide (0.15 eq) in ethanol (15 ml) was refluxed for 24 h. The residue was treated with saturated NH$_4$Cl (10 mL), extracted with ethylacetate (3×25 mL). The combined organic layer was washed with H$_2$O (10 mL), brine (10 mL), dried over Na$_2$SO$_4$, evaporated to dryness and purified by silica gel (100-200 mesh) using ethylacetate:Pet ether (10:90) as a mobile phase to give 7 (3.8 g, 73%) as off white solid. $^1$H NMR (200 MHz, CDCl$_3$): δ 7.90-7.94 (d, 2H), 7.41-7.46 (d, 2H), 3.20-3.27 (t, 2H), 2.86-2.97 (t, 2H), 2.26 (s, 3H).

1,2-bis(4-chlorophenyl)-5-methyl-1H-pyrrole (8)

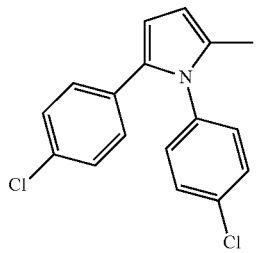

(8)

The mixture of 1,4-dione (2) (2 g, 1 eq), 4-chloroaniline (1.0 eq), and catalytic amounts of TsOH.H$_2$O, (2.0 mol %) in toluene (50 ml) was refluxed in a flask equipped with a Dean-Stark apparatus for 8 h. After cooling, the dark-brown reaction mixture was concentrated in vacuo. Purification by silica gel (100-200 mesh) using ethylacetate:Pet ether (2:98) as a mobile phase to provide the desired N-aryl pyrrole derivative 8 (2.2 g, 79%). $^1$H NMR (200 MHz, CDCl$_3$): δ 7.37-7.33 (d, 2H), 7.12-7.08 (m, 4H), 6.93-6.98 (d, 2H), 6.34-6.33 (d, 1H), 6.10-6.08 (d, 1H), 2.13 (s, 3H).

Procedure A: 1-((1,5-bis(4-chlorophenyl)-2-methyl-1H-pyrrol-3-yl)methyl)-4,4-dimethyl-1,4-azasilinane (9)

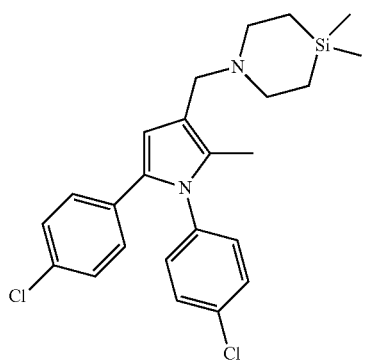

(9)

To a solution of 4,4-dimethyl-1,4-azasilinane hydrochloride (100 mg, 1 eq) in acetonitrile (5 ml), triethylamine (1.1 eq) was added, stirred for 30 min at ambient temperature and then formaldehyde (40% solution, 1 eq) and acetic acid (2 ml) was added, stirred for 10 min at room temperature. This mixture was added to a solution of 1,2-bis(4-chlorophenyl)-5-methyl-1H-pyrrole (8) (1 eq) in acetonitrile:aceticacid (5:1; 6 mL) at 0° C., stirred for 8 h at room temperature. Residue was then basified with solution of NaOH (20%, w/v) and extracted with ethylacetate (3×10 mL). The organic extracts were combined, washed with water (10 mL), and dried over Na$_2$SO$_4$. After removal of solvent, residue was purified by silica gel (230-400 mesh) using ethanol: DCM (3:97) as mobile phase or through reverse phase column (C18) using H$_2$O:MeOH:DIP (Diiso propyl amine) to afford 9 (30 mg, 12%) as white solid. $^1$H NMR (400 MHz, CDCl3) δ ppm 7.38 (m, J=8.5 Hz, 2H), 7.20-7.04 (m, 4H), 6.95 (d, J=8.3 Hz, 2H), 6.56 (s, 1H), 4.09 (s, 2H), 3.36 (m, 4H), 2.16 (s, 3H), 1.30 (m, 4H), 0.18 (s, 6H). $^{13}$C NMR (100 MHz, CDCl3) δ ppm 136.8, 134.1, 133.4, 132.8, 132.5, 130.4, 129.6, 129.5, 129.1, 128.4, 111.6, 108.6, 52.9, 51.5, 11.6, 10.6, −3.8; MS: 466 (M+Na)$^+$ All diaryl substituted pyrrole were prepared using known methods, Mannich reaction was performed using formaldehyde and 4,4-dimethyl-1,4-azasilinane hydrochloride (1.21 mmol) using Procedure A to yield following compounds.

Example 3

1-((1-(4-fluorophenyl)-2-methyl-5-(4-(methylthio) phenyl)-1H-pyrrol-3-yl)methyl)-4,4-dimethyl-1,4-azasilinane (10a)

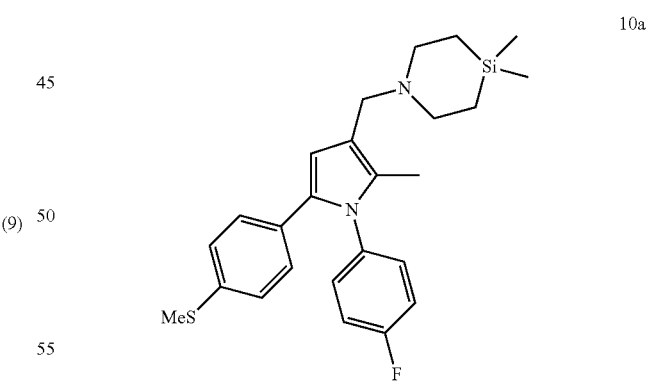

10a

Yield (0.25 g crude; 1:0.7:10a:10b); $^1$H NMR (400 MHz, CDCl$_3$) δ ppm 7.16-7.05 (m, 6H), 6.97 (d, J=8.2 Hz, 2H), 6.40 (s, 1H), 3.56 (s, 2H), 2.84 (m, 4H), 2.45 (s, 3H), 2.08 (s, 3H), 0.87 (t, J=5.6 Hz, 4H), 0.09 (s, 6H). $^{13}$C NMR (100 MHz, CDCl$_3$) δ ppm 161.6 (d, J=247.9 Hz, 1C), 135.5, 135.4, 132.7, 130.8, 130.1 (d, J=8.5 Hz, 1C), 130.03, 129.97, 128.0, 126.0, 116.0 (d, J=22.9 Hz, 1C), 110.9, 54.4, 52.2, 15.8, 13.5, 11.2, −3.1; MS: 439.1 (M+H)$^+$.

Example 4

1-((1-(4-fluorophenyl)-5-methyl-2-(4-(methylthio)phenyl)-1H-pyrrol-3-yl)methyl)-4,4-dimethyl-1,4-azasilinane (10b)

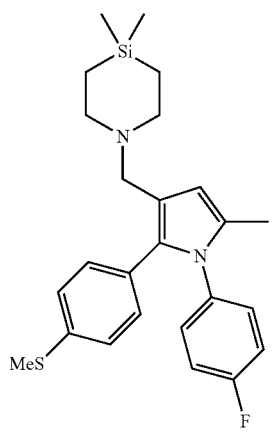

¹H NMR (400 MHz, CDCl₃) δ ppm 7.06-6.97 (m, 8H) 6.14 (s, 1H) 3.43 (s, 2H) 2.68 (t, J=6.5 Hz, 4H) 2.43 (s, 3H) 2.10 (s, 3H) 0.73 (t, J=6.3 Hz, 4H) 0.02 (s, 6H), ¹³C NMR (100 MHz, CDCl₃) δ ppm 161.3 (d, J=246.6 Hz, 1C), 136.2, 135.2, 131.7, 130.8, 130.0, 129.9 (d, J=8.5 Hz, 1C), 129.4, 125.7, 115.6 (d, J=23.1 Hz, 1C), 109.4, 54.2, 52.1, 15.5, 13.6, 13.1, −3.01. MS: 477.03 (M+K)⁺

Example 5

1-((1-(4-chlorophenyl)-5-(4-isopropylphenyl)-2-methyl-1H-pyrrol-3-yl)methyl)-4,4-dimethyl-1,4-azasilinane (11a)

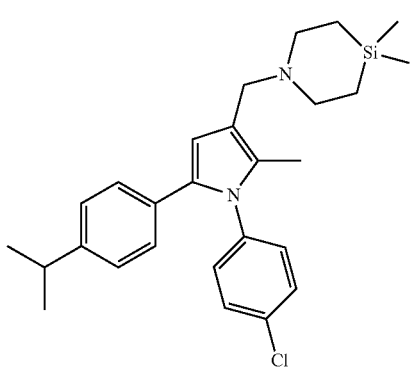

Yield (0.43 g crude); ¹H NMR (400 MHz, CDCl₃) δ ppm 7.34-7.32 (m, 2H), 7.11-6.94 (m, 6H), 6.36 (s, 1H), 3.62 (s, 2H), 2.89-2.78 (m, 5H), 2.07 (s, 3H), 1.19 (d, J=6.9 Hz, 6H), 0.89 (t, J=6.0 Hz, 4H), 0.07 (s, 6H), ¹³C NMR (100 MHz, CDCl₃) δ ppm=146.5, 130.0, 133.4, 133.1, 130.3, 129.8, 129.6, 129.1, 128.8, 127.5, 126.1, 110.9, 54.2, 52.0, 33.6, 23.8, 13.2, 11.3, −3.2; MS: 473.01 (M+Na)⁺

Example 6

1-((1-(4-isopropylphenyl)-2-methyl-5-(4-(methylthio)phenyl)-1H-pyrrol-3-yl)methyl)-4,4-dimethyl-1,4-azasilinane (12a)

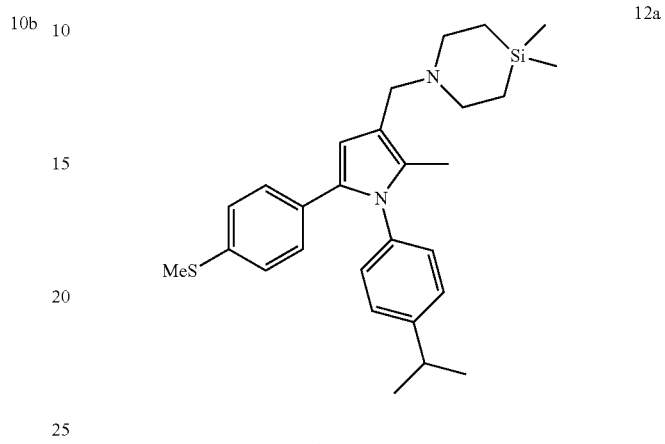

Yield (0.52 g crude); ¹H NMR (400 MHz, CDCl₃) δ ppm 7.22-7.19 (m, 2H), 7.07-6.94 (m, 6H), 6.36 (s, 1H), 3.53 (s, 2H), 2.94 (sep, J=7.3 Hz, 1H), 2.80 (t, J=6.0 Hz, 4H), 2.41 (s, 3H), 2.06 (s, 3H), 1.27 (d, J=6.9 Hz, 6H), 0.82 (t, J=6.4 Hz, 4H), 0.05 (s, 6H); ¹³C NMR (100 MHz, CDCl₃) δ ppm 148.1, 137.0, 134.9, 132.4, 130.8, 130.5, 130.0, 128.3, 127.8, 126.9, 126.2, 110.6, 54.2, 52.1, 33.7, 24.0, 15.7, 13.5, 11.3, −3.0; 485.02 (M+Na)⁺

Example 7

1-((1-(4-isopropylphenyl)-5-methyl-2-(4-(methylthio)phenyl)-1H-pyrrol-3-yl)methyl)-4,4-dimethyl-1,4-azasilinane (12b)

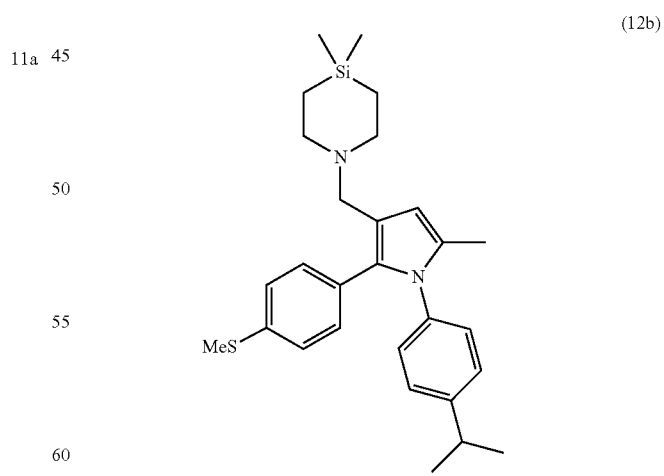

¹H NMR (400 MHz, CDCl₃) δ ppm 7.13-7.11 (m, 2H), 7.05-6.95 (m, 6H), 6.14 (s, 1H), 3.46 (s, 2H), 2.88 (sep, J=6.8 Hz, 1H), 2.69 (t, J=6.4 Hz, 4H), 2.43 (s, 3H), 2.11 (s, 3H), 1.22 (d, J=6.8 Hz, 6H), 0.74 (t, J=6.4 Hz, 4H), 0.02 (s, 6H); ¹³C NMR (100 MHz, CDCl₃) δ ppm 147.6, 136.7, 135.8, 131.8, 130.9, 130.0, 129.9, 128.2, 126.7, 125.6, 109.1, 54.2, 52.1, 33.7, 24.0, 15.7, 13.5, 13.3, −2.9; MS: 485.02 (M+Na)⁺

Example 8

1-((5-(4-chlorophenyl)-1-(4-ethylphenyl)-2-methyl-1H-pyrrol-3-yl)methyl)-4,4-dimethyl-1,4-azasilinane (13)

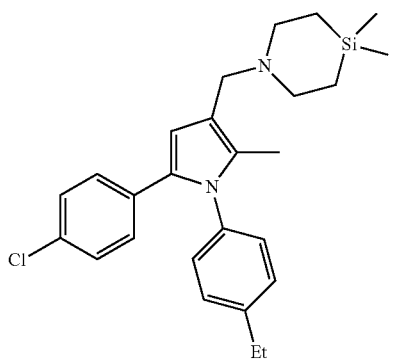

(13)

yield (0.43 g crude); $^1$H NMR (400 MHz, CDCl$_3$) δ ppm 7.21 (d, J=8.3 Hz, 2H), 7.10 (d, J=8.5 Hz, 2H), 7.03 (d, J=8.1 Hz, 2H), 6.96 (d, J=8.5 Hz, 2H), 6.53 (s, 1H), 4.12 (s, 2H), 3.67 (m, 2H), 3.03 (m, 2H), 2.69 (q, J=7.6 Hz, 2H), 2.13 (s, 3H), 1.62 (m, 2H), 1.26 (t, J=7.6 Hz, 3H), 0.94 (m, 2H), 0.18 (s, 6H); $^{13}$C NMR (100 MHz, CDCl$_3$)-δ ppm 144.5, 135.8, 133.5, 133.1, 132.1, 130.8, 128.9, 128.7, 128.2, 128.1, 111.1, 107.8, 53.3, 51.5, 28.4, 15.3, 11.6, 10.7, −0.4; MS: 437.15 (M+H)⁺

Example 9

1-((1-(4-fluorophenyl)-2-(4-methoxyphenyl)-5-methyl-1H-pyrrol-3-yl)methyl)-4,4-dimethyl-1,4-azasilinane (14)

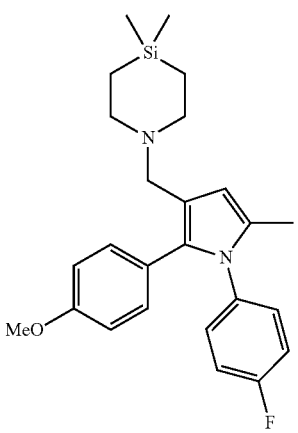

(14)

Yield (0.30 g crude); $^1$H NMR (400 MHz, CDCl$_3$) δ ppm 7.04-6.94 (m, 6H), 6.71 (d, J=8.2 Hz, 2H), 6.13 (s, 1H), 3.75 (s, 3H), 3.42 (s, 2H), 2.66 (t, J=6.4 Hz, 4H), 2.10 (s, 3H), 0.72 (t, J=6.4 Hz, 4H), 0.01 (s, 6H); $^{13}$C NMR (100 MHz, CDCl$_3$) δ=161.2 (d, J=247.0 Hz), 157.9, 135.3, 132.0, 131.8, 129.9 (d, J=8.6 Hz), 129.2, 125.2, 118.3, 115.4 (d, J=21.9 Hz), 113.1, 108.9, 55.1, 54.2, 52.1, 13.6, 13.1, −3.0; MS: 461.03 (M+K)⁺

Example 10

1-((5-(4-chlorophenyl)-2-methyl-1-phenyl-1H-pyrrol-3-yl)methyl)-4,4-dimethyl-1,4-azasilinane (15)

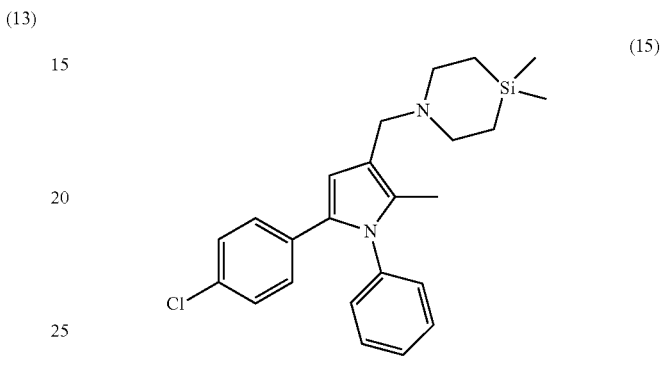

(15)

Yield (0.39 g crude); NMR (400 MHz, CDCl$_3$) δ ppm 7.37 (m, 3H), 7.15 (m, 2H), 7.08 (m, 2H), 6.97 (m, 2H), 6.41 (s, 1H), 3.53 (s, 2H), 2.80 (m, 4H), 2.08 (m, 3H), 0.83 (m, 4H), 0.07 (s, 6H); $^{13}$C NMR (100 MHz, CDCl$_3$) δ ppm=139.2, 131.8, 131.7, 131.1, 130.2, 129.0, 128.6, 128.5, 128.0, 127.5, 117.3, 111.2, 54.5, 52.2, 13.7, 11.2, −3.1; MS: 410.64 (M+H)⁺.

Example 11

1-((5-(4-ethylphenyl)-1-(4-methoxyphenyl)-2-methyl-1H-pyrrol-3-yl)methyl)-4,4-dimethyl-1,4-azasilinane (16)

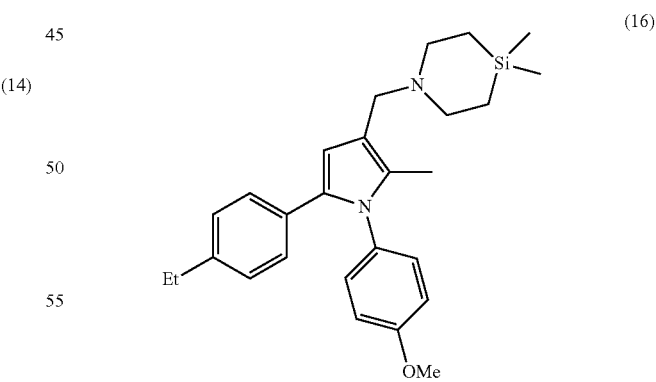

(16)

Yield (0.43 g crude); $^1$H NMR (400 MHz, CDCl$_3$) δ ppm 7.08 (m, 2H), 6.97 (m, 4H), 6.87 (m, 2H), 6.34 (s, 1H), 3.82 (s, 3H), 3.58 (s, 2H), 2.84 (t, J=6.4 Hz, 4H), 2.55 (q, J=7.8 Hz, 2H), 2.05 (s, 3H), 1.17 (t, J=7.8 Hz, 3H), 0.86 (t, J=6.2 Hz, 4H), 0.06 (s, 6H); $^{13}$C NMR (100 MHz, CDCl$_3$) δ 158.6, 141.5, 133.3, 132.5, 130.8, 130.5, 130.1, 129.7, 129.5, 127.5, 114.1, 110.3, 55.5, 54.6, 52.1, 28.4, 15.4, 13.5, 11.3, −3.0; MS: 471.19 (M+K)⁺.

Example 11

1-((1-(4-fluorophenyl)-2-methyl-5-(p-tolyl)-1H-pyrrol-3-yl)methyl)-4,4-dimethyl-1,4-azasilinane (17)

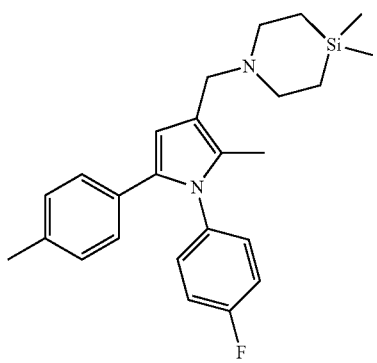

Yield (0.36 g crude); ¹H NMR (400 MHz, CDCl₃) δ=7.17-7.11 (m, 2H), 7.09-7.02 (m, 2H), 6.98-6.92 (m, 4H), 6.36 (s, 1H), 3.53 (s, 2H), 2.85-2.76 (t, J=6.4 Hz, 4H), 2.27 (s, 3H), 2.07 (s, 3H), 0.89-0.78 (t, J=6.4 Hz, 4H), 0.07 (s, 6H); ¹³C NMR (100 MHz, CDCl₃) δ=161.5 (d, J=247.3 Hz), 135.6, 135.3, 133.1, 130.3, 130.1 (d, J=8.6 Hz), 129.4, 128.7, 127.6, 116.9, 115.8 (d, J=23.0 Hz), 110.5, 54.5, 52.1, 21.0, 13.7, 11.2, −3.1; MS: 429 (M+Na)⁺.

Example 12

1-((2-(4-ethoxyphenyl)-1-(4-methoxyphenyl)-5-methyl-1H-pyrrol-3-yl)methyl)-4,4-dimethyl-1,4-azasilinane (18)

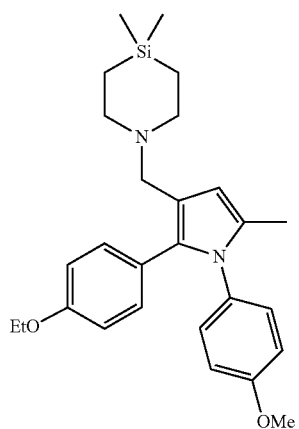

Yield (0.49 g crude); ¹H NMR (400 MHz, CDCl₃) δ ppm 6.99-6.96 (m, 4H), 6.78 (m, 2H), 6.70 (m, 2H), 6.12 (s, 1H), 3.96 (q, J=6.9 Hz, 2H), 3.77 (s, 3H), 3.47 (s, 2H), 2.69 (t, J=6.4 Hz, 4H), 2.09 (s, 3H), 1.37 (t, J=6.9 Hz, 3H), 0.74 (t, J=6.4 Hz, 4H), 0.01 (s, 6H); ¹³C NMR (100 MHz, CDCl₃) δ ppm 158.2, 157.4, 132.4, 132.2, 131.9, 131.6, 129.52, 129.48, 125.4, 113.8, 113.7, 108.6, 63.3, 55.4, 54.2, 52.1, 14.9, 13.5, 13.2, −2.9; MS: 471.07 (M+Na)⁺.

Example 12

1-((5-(4-chlorophenyl)-1-(4-isopropylphenyl)-2-methyl-1H-pyrrol-3-yl)methyl)-4,4-dimethyl-1,4-azasilinane (19)

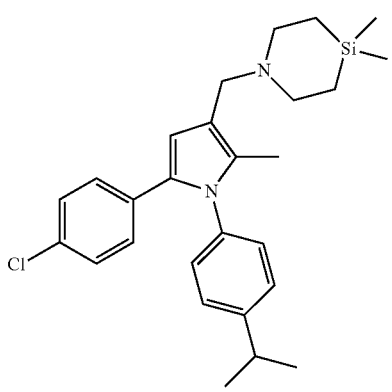

Yield (0.50 g crude); ¹H NMR (400 MHz, CDCl₃) δ=7.24-7.19 (m, 2H), 7.10-7.03 (m, 4H), 6.99-6.93 (m, 2H), 6.41-6.36 (s, 1H), 3.49 (s, 2H), 2.95 (spt, J=6.9 Hz, 1H), 2.81-2.73 (t, J=6.4 Hz, 4H), 2.07 (s, 3H), 1.31-1.24 (d, J=6.9 Hz, 6H), 0.84-0.77 (t, J=6.4 Hz, 4H), 0.08-0.04 (m, 6H); ¹³C NMR (101 MHz, CDCl₃) δ=148.2, 136.8, 132.0, 131.7, 131.0, 130.3, 128.5, 128.3, 128.0, 127.0, 117.4, 111.0, 54.6, 52.2, 33.7, 23.9, 13.8, 11.2, −3.0; MS: 451.06 (M+H)⁺.

Example 12

Anti Tubercular Activity of Selected Compounds

The compounds were tested for antitubercular activity through inhibition of growth of the virulent strain of *Mycobacterium tuberculosis* $H_{37}Rv$ using Alamar-Blue assay method. MIC (Minimum Inhibitory Concentration) values of the compounds against $H_{37}Rv$ were determined in 7H9-OADC media supplemented with 0.5% glycerol and 1 mg ml⁻¹ tryptone at 37° C. in 96-well microtiter plates using the colorimetric resazurin microtiter assay, and growth was measured by visual readout. Rifampicin was used as a positive drug control. The MIC for BM212 and rifampicin are 0.7 and 0.25 µg/ml according to literature (Biava. M et. al; J. Med. Chem 2008; 51; 3644).

TABLE 1

| Compound No. | MIC (µg/ml) |
|---|---|
| 9 | 0.04 |
| 10a | 0.08 |
| 10b | 1.56 |
| 11a | 0.04 |
| 12a | 0.04 |
| 12b | 1.25 |
| 13 | 0.08 |
| 14 | 3.12 |
| 15 | 0.04 |
| 16 | 0.08 |
| 17 | 0.04 |
| 18 | 5 |
| 19 | 0.04 |
| BM212 | 1.56 |

ADVANTAGES OF THE INVENTION

Sila analogs are alternative to existing therapy for *tuberculosis*.

Compound has better physico-chemical properties, in particular lipophilicity and in vivo metabolism, which in turn may lead to potential drug candidates with improved brain penetration and better safety profile (cf *J. Med. Chem.* 2013, 56, 388-405; *Expert Opin. Investig. Drugs* 2004, 13 (9): 1149-1157).

Process to synthesize the compound is economical and commercially feasible.

The invention claimed is:

1. A novel silicon incorporated pyrrole compounds of Formula I and or pharmaceutically acceptable salts thereof

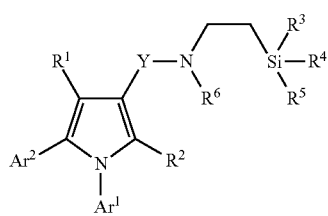

(I)

wherein $R^1$ and $R^2$ are selected from hydrogen, halogen, alkyl, haloalkyl, hydroxyalkyl, thioalkyl, aryl, heteroaryl, C1-C5 alkoxy, C1-C5 alkoxyalkyl, —NR'R", —CH$_2$NR'R"—CONR'R", —COOR'";

R', R" are independently selected from hydrogen or alkyl, aryl which may be substituted or unsubstituted or R' and R" together may form a ring up to six carbon atoms which optionally may be substituted and/or may contain hetero atoms;

R'" is selected from hydrogen or alkyl, aryl which may be substituted or unsubstituted;

$R^3$, $R^4$ and $R^5$ each are individually selected from alkyl;

$R^6$ is selected from hydrogen, alkyl, or $R^6$ together with any of $R^3$, $R^4$ and $R^5$ may form a ring;

$Ar^1$ and $Ar^2$ represent independently a aryl or heteroaryl unsubstituted, or substituted with one or more substituents selected independently from halo, hydroxy, alkyl, aralkyl, cycloalkyl, alkoxy, alkylthio, alkyl sulfinyl, alkyl sulfonyl, heterocyclyl, aryl, nitro, sulfonyl, —NR'R", —CONR'R", —COOR'" wherein positions of substituent $Ar^2$ and $R^2$ are interchangeable;

Y represents CO, CS, CONH or $CR^1R^2$; wherein $R^1R^2$ are independently selected from hydrogen or alkyl, aryl which may which may be substituted or unsubstituted; or $R^1$ and $R^2$ together form a ring up to six carbon atoms which optionally may be substituted and/or may contain hetero atoms.

2. The novel silicon incorporated pyrrole compounds of Formula I—as claimed in claimed 1, wherein said compounds are selected from the group consisting of
a) (1,5-bis(4-chlorophenyl)-2-methyl-1H-pyrrol-3-yl)(4,4-dimethyl-1,4-azasilinan-1-yl) methanone of formula (5);
b) 1-((1,5-bis(4-chlorophenyl)-2-methyl-1H-pyrrol-3-yl) methyl)-4,4-dimethyl-1,4-azasilinane of formula (9);
c) 1-((1-(4-fluorophenyl)-2-methyl-5-(4-(methylthio) phenyl)-1H-pyrrol-3-yl)methyl)-4,4-dimethyl-1,4-azasilinane(10a);
d) 1-((1-(4-fluorophenyl)-5-methyl-2-(4-(methylthio) phenyl)-1H-pyrrol-3-yl)methyl)-4,4-dimethyl-1,4-azasilinane(10b);
e) 1-((1-(4-chlorophenyl)-5-(4-isopropylphenyl)-2-methyl-1H-pyrrol-3-yl)methyl)-4,4-dimethyl-1,4-azasilinane(11a);
f) 1-((1-(4-isopropylphenyl)-2-methyl-5-(4-(methylthio) phenyl)-1H-pyrrol-3-yl)methyl)-4,4-dimethyl-1,4-azasilinane(12a);
g) 1-((1-(4-isopropylphenyl)-5-methyl-2-(4-(methylthio) phenyl)-1H-pyrrol-3-yl)methyl)-4,4-dimethyl-1,4-azasilinane(12b);
h) 1-((5-(4-chlorophenyl)-1-(4-ethylphenyl)-2-methyl-1H-pyrrol-3-yl)methyl)-4,4-dimethyl-1,4-azasilinane (13);
i) 1-((1-(4-fluorophenyl)-2-(4-methoxyphenyl)-5-methyl-1H-pyrrol-3-yl)methyl)-4,4-dimethyl-1,4-azasilinane (14);
j) 1-((5-(4-chlorophenyl)-2-methyl-1-phenyl-1H-pyrrol-3-yl)methyl)-4,4-dimethyl-1,4-azasilinane(15);
k) 1-((5-(4-ethylphenyl)-1-(4-methoxyphenyl)-2-methyl-1H-pyrrol-3-yl)methyl)-4,4-dimethyl-1,4-azasilinane (16);
l) 1-(0-(4-fluorophenyl)-2-methyl-5-(p-tolyl)-1H-pyrrol-3-yl)methyl)-4,4-dimethyl-1,4-azasilinane(17);
m) 1-((2-(4-ethoxyphenyl)-1-(4-methoxyphenyl)-5-methyl-1H-pyrrol-3-yl)methyl)-4,4-dimethyl-1,4-azasilinane(18);
n) 1-((5-(4-chlorophenyl)-1-(4-isopropylphenyl)-2-methyl-1H-pyrrol-3-yl)methyl)-4,4-dimethyl-1,4-azasilinane(19).

3. The Silicon incorporated pyrrole compounds of Formula I as claimed in claim 1, wherein said compounds are useful for the treatment of *tuberculosis* particularly against *Mycobacterium tuberculosis* both in dormant or latent phase.

4. A process for preparation of novel pyrrole compounds with silicon incorporation Formula I as claimed in claim 1 comprising;

peptide coupling of compound of formula A,

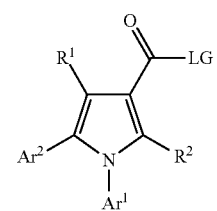

A wherein $R^1$ and $R^2$ are selected from hydrogen, halogen, alkyl, haloalkyl, hydroxyalkyl, thioalkyl, aryl, heteroaryl, C1-C5 alkoxy, C1-C5 alkoxyalkyl, —NR'R", —CH$_2$NR'R"—CONR'R", —COOR'";

R', R" are independently selected from hydrogen or alkyl, aryl which may be substituted or unsubstituted or R' and R" together may form a ring up to six carbon atoms which optionally may be substituted and/or may contain hetero atoms;

R'" is selected from hydrogen or alkyl, aryl which may be substituted or unsubstituted;

$Ar^1$ and $Ar^2$ represent independently a aryl or heteroaryl unsubstituted, or substituted with one or more substituents selected independently from halo, hydroxy, alkyl, aralkyl, cycloalkyl, alkoxy, alkylthio, alkyl sulfinyl, alkyl sulfonyl, heterocyclyl, aryl, nitro, sulfonyl, —NR'R", —CONR'R", —COOR'" wherein positions of substituent Ar² and R² are interchangeable;

LG represent the leaving group selected from —OH, halogen and anhydride;

with an amine of formula B

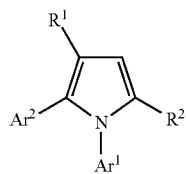

wherein, M is selected from H or —NH2;

R³, R⁴ and R⁵ each are individually selected from alkyl; R⁶ is selected from hydrogen, or R⁶ together with any of R³, R⁴ and R⁵ may form a ring;

in presence of a coupling agent, HOBt, a base and solvent at a temperature in the range of 55-65° C.

5. A process for preparation of novel pyrrole compounds with silicon incorporation of Formula I as claimed in claim 1 comprising;

reacting pyrrole compound of Formula C

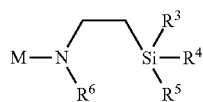

wherein, R¹ and R² are selected from hydrogen, halogen, alkyl, haloalkyl, hydroxyalkyl, thioalkyl, aryl, heteroaryl, C1-C5 alkoxy, C1-C5 alkoxyalkyl, —NR'R", —CH₂NR'R"—CONR'R", —COOR'";

R', R" are independently selected from hydrogen or alkyl, aryl which may be substituted or unsubstituted or R' and R" together may form a ring up to six carbon atoms which optionally may be substituted and/or may contain hetero atoms;

R'" is selected from hydrogen or alkyl, aryl which may be substituted or unsubstituted;

Ar¹ and Ar² represent independently a aryl or heteroaryl unsubstituted, or substituted with one or more substituent selected independently from halo, hydroxy, alkyl, aralkyl, cycloalkyl, alkoxy, alkylthio, alkyl sulfinyl, alkyl sulfonyl, heterocyclyl, aryl, nitro, sulfonyl, —NR'R", —CONR'R", —COOR'" wherein positions of substituent Ar² and R are interchangeable;

with a compound of formula B;

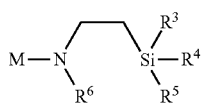

wherein, M is selected from H or —NH2; R³, R⁴ and R⁵ each are individually selected from alkyl; R⁶ is selected from hydrogen, or R⁶ together with any of R³, R⁴ and R⁵ may form a ring;

in presence of formaldehyde, base and a solvent at room temperature for a time period ranging between 16 to 18 hours.

6. The process according to claim 4, wherein the coupling agent is selected from N,N'-Dicyclohexylcarbodiimide (DCC),1-Ethyl-3-(3-dimethylaminopropyl)carbodiimide (EDC), HATU (0-(7-azabenzotriazol-1-yl)-N,N,N',N'-tetramethyluronium hexafluorophosphate), and HBTU (0-Benzotriazole-N,N,N',N'-tetramethyl-uronium-hexafluoro-phosphate).

7. The process according to claim 4, wherein the base is selected from ethylamine, diethylamine, triethylamine, and pyridine.

8. The process according to claim 4, wherein the solvent is selected from polar protic or aprotic solvents either alone or mixtures thereof.

9. A pharmaceutical composition comprising a pharmaceutically acceptable excipient and an effective amount of a compound of Formula I, according to claim 1 for the treatment of *tuberculosis*.

\* \* \* \* \*